United States Patent [19]

Sandel

[11] 4,013,109
[45] Mar. 22, 1977

[54] DISPOSABLE CONTAINER FOR SURGICAL INSTRUMENTS
[76] Inventor: Dan Sandel, 17000 Cotter Place, Encino, Calif. 91316
[22] Filed: Aug. 22, 1975
[21] Appl. No.: 606,792
[52] U.S. Cl. .............................. 150/52 R; 206/63.3; 206/350; 206/818
[51] Int. Cl.² ........................................ A61L 17/02
[58] Field of Search ............ 128/1.3; 206/63.3, 234, 206/339, 350, 365, 366, 380, 818; 150/52 R, 34

[56] References Cited
UNITED STATES PATENTS

| | | | |
|---|---|---|---|
| 3,727,658 | 4/1973 | Eldridge | 150/52 R |
| 3,759,376 | 9/1973 | Lisowski | 206/63.3 |
| 3,779,375 | 12/1973 | Foster | 206/63.3 |
| 3,940,873 | 3/1976 | Lawless | 150/52 R |
| 3,944,069 | 3/1976 | Eldridge | 206/350 |

Primary Examiner—Ro E. Hart
Attorney, Agent, or Firm—Poms, Smith, Lande & Glenny

[57] ABSTRACT

A hinged sterilizable disposable container for magnetizable surgical instruments which has relatively large upper and lower portions connected by sides of a relatively narrower dimension. A non-deformable outer case is provided for retaining the instruments entirely within the case and precluding any tendencies for said instruments to protrude from the case. Magnetic means are provided which completely cover the interior portion of the case and retain any magnetizable instruments placed within the case.

7 Claims, 3 Drawing Figures

DISPOSABLE CONTAINER FOR SURGICAL INSTRUMENTS

BACKGROUND OF THE INVENTION

Each surgical procedure requires the use of small, sharp surgical instruments, such as needles, knives, staples and the like. Medical requirements dictate that strict inventory control will be performed during the use of these instruments in order to prevent any of these instruments from being left within the human body after the closure of the incision. Most of the present instruments are disposable and considered contaminated after use and should be discarded safely. Therefore, strict and exact accountability and a safe method of disposing of each and every instrument is required. In addition to the safety requirements for the patient and the operating room personnel, in the case of a dropped instrument, resterilization is required prior to use.

In the past, attempts have been made to utilize magnetic devices to hold the instruments within a control area:

United States Patent No. 3,727,658 — Eldridge (1973), utilizes magnetic strips on a foam pad. The entire assembly is sealed within a plastic cover sheet. This assembly may be rather easily pierced or cut by the sharp surgical instruments resulting in a potential danger of lost instruments or injury to operating room personnel. Further, when in use, the device requires that instruments be placed directly upon the magnetic strips and not the adjacent foam areas, otherwise the device will not retain the instrument. Additionally, unless an adhesive material is placed along the periphery of the pad for edge sealing purposes, it is possible for instruments to be dislodged from the pad and become lost once the pad is folded. Such an adhesive would present a serious contamination problem in a sterile environment, and would also inconvenience the user as the adhesive sticks to surgical latex gloves.

United States Patent No. 3,546,643 — Virostek (1970), teaches the use of a perforated rubber mat with magnetics placed in the perforations and an outer sealing skin enclosing the entire assembly. This results in a complex, expensive device which must be re-used repeatedly.

The present invention addresses itself generally to a hinged sterilizable disposable container for magnetizable instruments. It is considered of primary importance to assure the total containment of the instruments within the container, thereby eliminating problems of loss or danger of injury to operating personnel during the handling and discarding of such instruments. Further, the container must be economical and convenient to use.

SUMMARY OF THE INVENTION

Therefore it is a primary objective of the present invention to disclose and provide an improvement in instrument cases for magnetizable instruments, whereby a non-deformable outer case retains the instruments entirely therewithin, thereby eliminating any tendencies for the instruments to protrude from the case, become lost and/or injure the user.

It is a further objective of the present invention to disclose and provide magnetic means within the case for retaining any magnetizable instruments placed within the case. The magnetic means cover the entire lower interior portion of the case making it impossible for an instrument placed within the case to avoid retention by the magnetic means.

Additionally, the magnetic means may be attached to and completely cover an upper interior portion of the case such that, upon opening the case, both magnetic means are exposed. This will result in an effective doubling of the surface area available to receive and retain any instruments placed thereon. This increase in size will make it less likely that personnel using the case will fail to place the instrument in contact with the magnetic means.

A still further objective of the present invention is to disclose and provide mechanical latch means for holding the case shut. This will alleviate the contamination problem and, more importantly, will eliminate the problem presented by an adhesive fastening system of a gloved hand sticking to the case. A still further objective of the present invention is to disclose and provide aperture means within the sides of the case such that suture material, and the like, attached to the instruments may pass out of the case.

An additional objective of the present invention is to disclose and provide non-planar surface means on the magnetic means for facilitating the grasping and removal of the instruments from the case.

DETAILED DESCRIPTION OF AN EXEMPLARY EMBODIMENT

Figure 2:
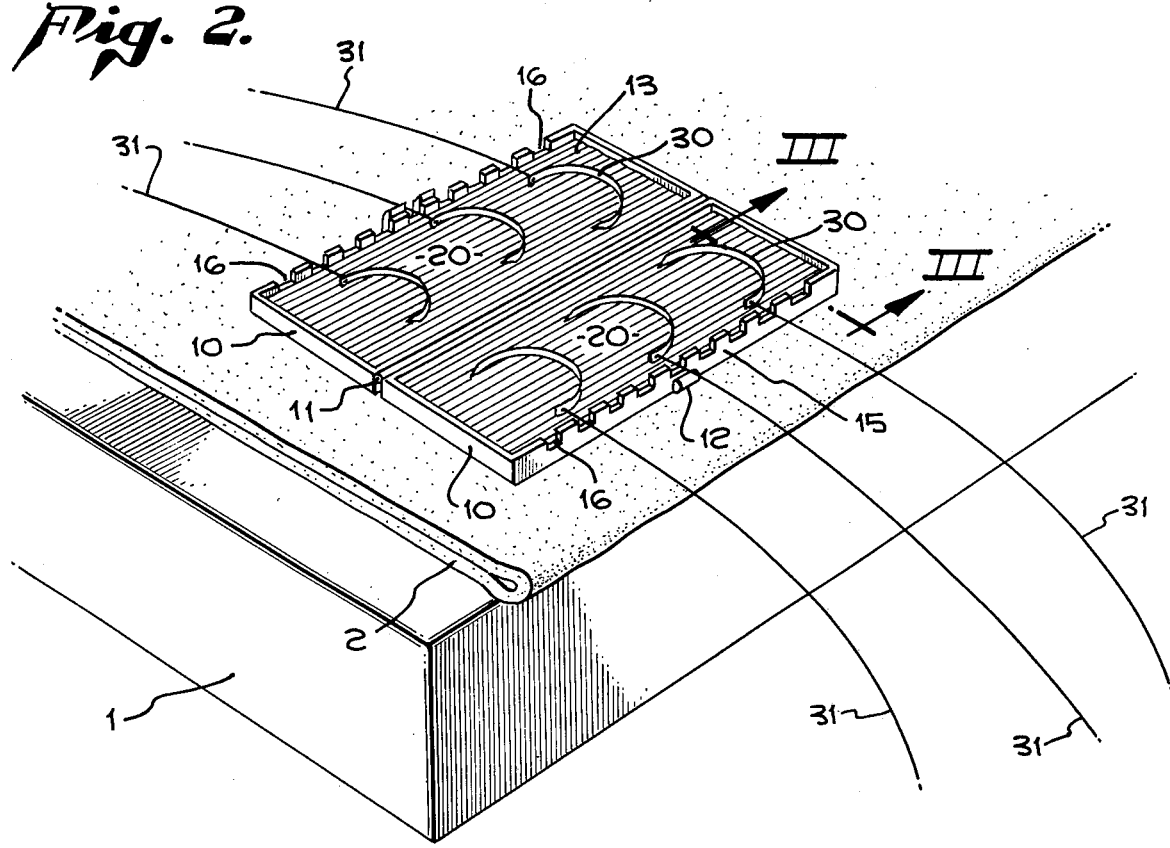
FIG. 2 is a perspective view of the case opened to expose the instruments.
Figure 3:
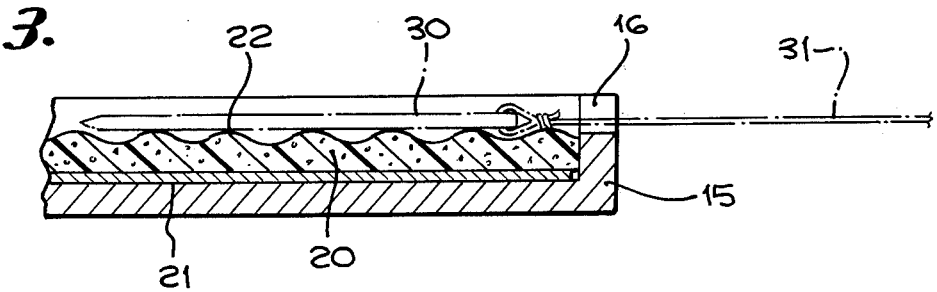
FIG. 3 is a partial and sectional view taken through the plane III—III of FIG. 2.

A hinged, sterilizable, disposable container for magnetizable instruments is shown in an opened configuration generally in FIG. 2. In the exemplary embodiment, the upper interior surface 13 and the lower interior surface are relatively larger than the side surfaces 15.

A non-deformable outer case 10 is provided for retaining the instruments in an entirely enclosed manner, thereby preventing any loss of instruments or injury to persons handling the case. In the exemplary embodiment, case 10 is fabricated from a rigid plastic material.

In the exemplary embodiment, said plastic material is colored red. This help identify the instruments contained within as potentially dangerous and contaminated. After use, such red case, being highly visible, may be safely and easily discarded according to special handling procedures used in every hospital for the disposal of contaminated material. Any color not contrasting with the surgical drapes may, by virtue of its lack of visibility, cause the case to be overlooked and to become and folded within the drapes during clean up after surgery. Thereafter it may be sent to the laundry area where it would increase the potential for additional injury and a spread of contamination.

Magnetic means 20 which completely cover lower interior portion 14 are attached thereto by an adhesive 21. The magnetic means retain any magnetizable instruments 30 placed thereon. Further, additional magnetic means 20 may be attached to, and completely cover, upper interior portion 13 opposite the magnetic means 20 which cover lower interior portion 14 of outer case 10. Whereby, upon opening the case, both magnetic means 20 are exposed and positioned adjacent each other (FIG. 2), such that the surface area available to receive and retain any instrument placed thereon is substantially increased. In the exemplary embodiment, low-cost light-weight magnetic means 20 are formed of nitrile rubber, or other suitable matrix material, imbedded with particles of ferric oxide, barium ferrite or other suitable ferromagnetic material. Exemplary of such magnetic means is "Magnaribbon", produced by Magna Vision Company, St. Louis, Mo. Similar products are manufactured by B. F. Goodrich and Minnesota Mining & Manufacturing Co.

Mechanical latch means 12 are provided for holding case 10 closed. In the exemplary embodiment, latch means 12 are integrally formed with the case 10.

Apertures slot means are provided within the sides of the case such that suture material, and the like, attached to the instruments may pass therethrough.

In those applications of the present invention wherein surgical suture needles are the instruments to be contained within the case, the aperture slot means 16 allow the attached sutures 31 to project from the case. Additionally, the apertures perform an organizing and sorting function in that the sutures and needles do not become intertwined or entangled while in the case. In the exemplary embodiment, aperture slot means 16 within sides 15 of case 10 allow sutures 31 to pass outside the case.

Figure 1:
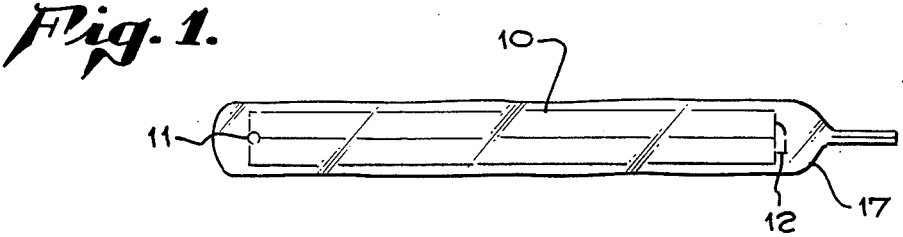
FIG. 1 is an end view showing the non-deformable outer case sealed within a sterile bag.

When in storage prior to use, the case, instruments and projecting sutures may be sealed under sterile conditions in a sterile plastic or paper envelope 17 (FIG. 1) for convenience and economy of time in the operating room.

Non-planar surface means are provided on the magnetic means for facilitating the grasping and removal of instruments from the case. In the exemplary embodiment, a series of grooves 22 are embossed into magnetic means 20. The grooves are shown to parallel and straight. However, any random pattern of surface irregularity would serve a similar function. In practice, such grooves might be approximately 0.020 inches deep and spaced approximately one-eight to one-fourth of an inch apart.

Although this invention has been described in detail with particular reference to certain exemplary embodiments, it is to be understood that various modifications thereof can be made by one skilled in the art and still come within the scope and spirit of the present invention which is only limited as defined in the appended claims.

I claim:

1. In a hinged sterilizable disposable container for magnetizable instruments having relatively large upper and lower portions connected by sides of a relatively narrow dimension, the improvement comprising:
   non-deformable case means for retaining said instruments entirely therewithin, said case means having upper and lower interior surfaces bounded by peripheral side wall means for enclosing the interior of said case means in a lateral direction when said upper and lower portions are hinged against each other, whereby any tendencies for said instruments to protrude through and therefrom are eliminated; and magnetic means attached to said lower interior surface of said case means for retaining any magnetizable instruments placed thereon.

2. In the hinged sterilizable disposable container of claim 1, the improvement further comprising:
   magnetic means attached to said upper interior portion opposite said lowerr interior portion such that, upon opening said case means, both magnetic means are exposed, whereby the surface area available to receive and retain any instruments placed thereon is substantially increased.

3. In the hinged sterilizable disposable container of claim 2, the improvement further comprising:
   the provision of said magnetic means attached to, and completely covering, said upper interior surface of said case means.

4. In the hinged sterilizable disposable container of claim 2, the improvement further comprising:
   the provision of said magnetic means attached to, and completely covering, both said lower interior surface and said upper interior surface of said case means.

5. In the hinged sterilizable disposable container of claim 1, the improvement further comprising:
   reusable mechanical latch means for releasably holding said case means upper and lower portions closed.

6. In the hinged sterilizable disposable container of claim 1, the improvement further comprising:
   aperture slot means within said sidewall means of said case means such that suture material and the like, attached to said instruments may pass therethrough.

7. In the hinged sterilizable disposable container of claim 1, the improvement further comprising:
   the provision of said magnetic means attached to, and completely covering, said lower interior surface of said case means.

* * * * *

Disclaimer

4,013,109.—*Dan Sandel*, Encino, Calif. DISPOSABLE CONTAINER FOR SURGICAL INSTRUMENTS. Patent dated Mar. 22, 1977. Disclaimer filed Jan. 29, 1981, by the inventor.

Hereby enters this disclaimer to claims 1, 2 and 5 of said patent.
[*Official Gazette April 14, 1981.*]

REEXAMINATION CERTIFICATE (2547th)

United States Patent [19]
Sandel

[11] B1 4,013,109
[45] Certificate Issued Apr. 25, 1995

[54] DISPOSABLE CONTAINER FOR SURGICAL INSTRUMENTS

[76] Inventor: Dan Sandel, 17000 Cotter Pl., Encino, Calif. 91316

Reexamination Request:
No. 90/002,983, Mar. 8, 1993

Reexamination Certificate for:
Patent No.: 4,013,109
Issued: Mar. 22, 1977
Appl. No.: 606,792
Filed: Aug. 22, 1975

[51] Int. Cl.⁶ .......................................... B65D 83/10
[52] U.S. Cl. .................. 206/370; 206/63.3; 206/350; 206/818
[58] Field of Search ............. 206/365, 366, 370, 818, 206/63.3

[56] References Cited

U.S. PATENT DOCUMENTS

| | | | |
|---|---|---|---|
| 361,248 | 4/1887 | Winton | 24/303 |
| 2,399,041 | 4/1946 | Kleber | 273/131 |
| 3,002,607 | 10/1961 | Laverty | 206/16 |
| 3,077,282 | 2/1963 | Eggers | 220/31 |
| 3,172,316 | 3/1965 | Grieshaber | 81/3 |
| 3,653,389 | 4/1972 | Shannon . | |
| 3,680,496 | 8/1972 | Westlake, Jr. . | |
| 3,723,061 | 3/1973 | Stahl | 206/370 |
| 3,798,836 | 3/1974 | Rubens et al. . | |
| 3,868,016 | 2/1975 | Szpur et al. . | |
| 4,008,802 | 2/1977 | Frietag | 206/63.3 |
| 4,034,892 | 7/1977 | Braginetz | 221/64 |

FOREIGN PATENT DOCUMENTS

129373   1/1901   Germany .

OTHER PUBLICATIONS

Creative Packaging Company Brochure, Catalog No. 769E, 1969, 37 pages.
Richard Wheatley & Sons advertisement, Dec. 1972.
Richard Wheatley & Sons advertisement, Nov. 1968, pp. 1 through 12.
A Comprehensive Guide to Purchasing, Mueller & Co., Catalog No. 65, 1963, 3 pages.

*Primary Examiner*—David T. Fidei

[57] ABSTRACT

A hinged sterilizable disposable container for magnetizable surgical instruments which has relatively large upper and lower portions connected by sides of a relatively narrower dimension. A non-deformable outer case is provided for retaining the instruments entirely within the case and precluding any tendencies for said instruments to protrude from the case. Magnetic means are provided which completely cover the interior portion of the case and retain any magnetizable instruments placed within the case.

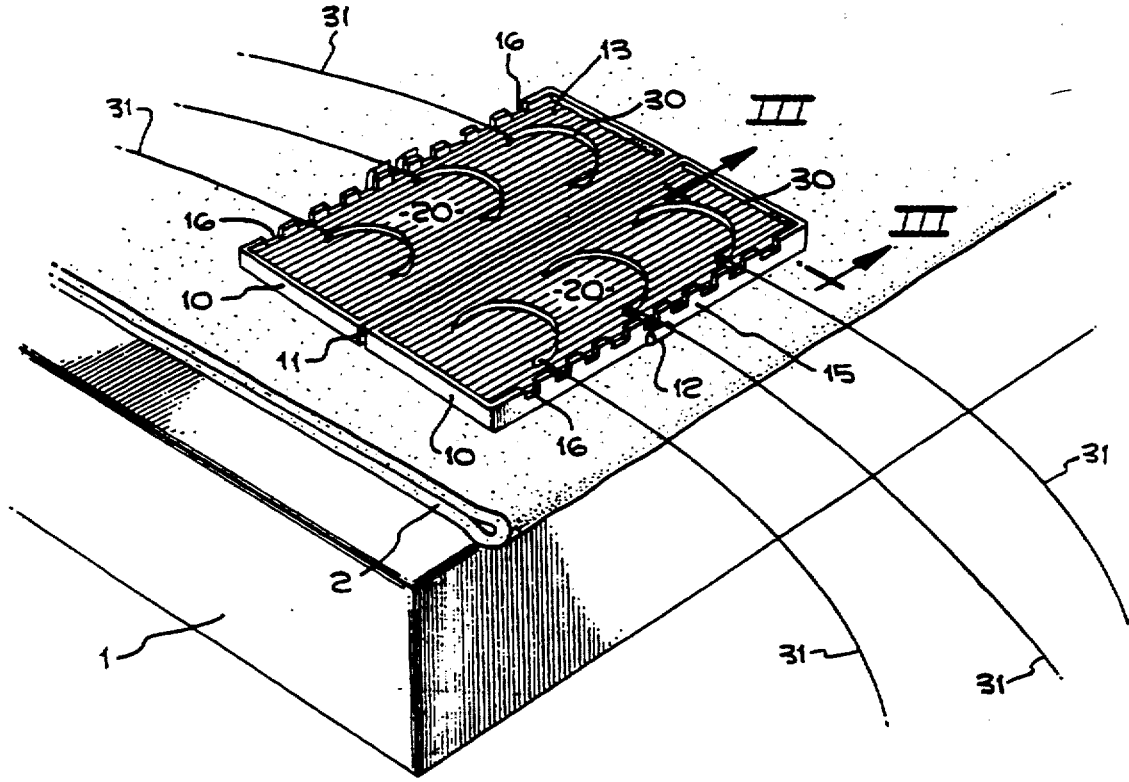

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 3, 4, 6 and 7 is confirmed.

Claims 1, 2 and 5 were previously disclaimed.

* * * * *